(12) United States Patent
Sabata

(10) Patent No.: US 11,432,807 B2
(45) Date of Patent: Sep. 6, 2022

(54) ULTRASOUND IMAGING SYSTEM, OPERATING METHOD OF ULTRASOUND IMAGING SYSTEM, AND COMPUTER-READABLE RECORDING MEDIUM

(71) Applicant: OLYMPUS CORPORATION, Tokyo (JP)

(72) Inventor: Tomohiro Sabata, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 297 days.

(21) Appl. No.: 16/901,145

(22) Filed: Jun. 15, 2020

(65) Prior Publication Data

US 2020/0305848 A1    Oct. 1, 2020

Related U.S. Application Data

(63) Continuation of application No. PCT/JP2018/047107, filed on Dec. 20, 2018.

(30) Foreign Application Priority Data

Dec. 20, 2017    (JP) .............................. JP2017-244257

(51) Int. Cl.
*A61B 8/00* (2006.01)
*A61B 8/08* (2006.01)
(Continued)

(52) U.S. Cl.
CPC ............ *A61B 8/5269* (2013.01); *A61B 8/145* (2013.01); *A61B 8/463* (2013.01); *A61B 8/469* (2013.01);
(Continued)

(58) Field of Classification Search
CPC ........ A61B 8/5269; A61B 8/145; A61B 8/463
See application file for complete search history.

(56) References Cited

FOREIGN PATENT DOCUMENTS

| JP | H09-000527 A | 1/1997 |
|---|---|---|
| JP | H09-313488 A | 12/1997 |

(Continued)

OTHER PUBLICATIONS

International Search Report dated Feb. 5, 2019 issued in PCT/JP2018/047107.

(Continued)

*Primary Examiner* — Joseph M Santos Rodriguez
(74) *Attorney, Agent, or Firm* — Scully, Scott, Murphy & Presser, P.C.

(57) ABSTRACT

Provided is an ultrasound imaging system configured to generate data of an ultrasound image based on an echo signal received by each of a plurality of elements included in an ultrasound transducer, the ultrasound imaging system includes: a determining circuit configured to determine, using a signal corresponding to the echo signal obtained by receiving from each of the plurality of elements, concerning the elements, whether a decrease in reception sensitivity occurs; and a control circuit configured to cause, based on a position of an element where the determining circuit determines that the decrease in the reception sensitivity occurs, a display to display at least one of display data indicating an image region where sensitivity decreases in the ultrasound image and information for informing that a sensitivity decreased element in which a decrease in reception sensitivity occurs is present.

13 Claims, 10 Drawing Sheets

(51) Int. Cl.
*A61B 8/14* (2006.01)
*G01S 7/53* (2006.01)
*G01S 7/56* (2006.01)
*G01S 15/89* (2006.01)

(52) U.S. Cl.
CPC .............. *A61B 8/5207* (2013.01); *A61B 8/54* (2013.01); *G01S 7/53* (2013.01); *G01S 7/56* (2013.01); *G01S 15/8906* (2013.01)

(56) References Cited

FOREIGN PATENT DOCUMENTS

| | | |
|---|---|---|
| JP | 2002-159492 A | 6/2002 |
| JP | 2008-220690 A | 9/2008 |
| JP | 2009-178262 A | 8/2009 |
| JP | 2013-165880 A | 8/2013 |
| JP | 2015-053961 A | 3/2015 |
| JP | 2015-097619 A | 5/2015 |

OTHER PUBLICATIONS

Japanese Office Action dated Jun. 22, 2021 received in 2017-244257.

ULTRASOUND IMAGING SYSTEM, OPERATING METHOD OF ULTRASOUND IMAGING SYSTEM, AND COMPUTER-READABLE RECORDING MEDIUM

CROSS-REFERENCE TO RELATED APPLICATION

This application is a continuation of PCT International Application No. PCT/JP2018/047107 filed on Dec. 20, 2018, which designates the United States, incorporated herein by reference, and which claims the benefit of priority from Japanese Patent Application No. 2017-244257, filed on Dec. 20, 2017, incorporated herein by reference.

BACKGROUND

1. Technical Field

The present disclosure relates to an ultrasound imaging system, an operating method of the ultrasound imaging system, and a computer-readable recording medium.

2. Related Art

In an ultrasound diagnosis system that performs diagnosis using an ultrasound probe, it has been requested to, every time the ultrasound probe is connected to an ultrasound observation device, inform a state of an ultrasound transducer included in the ultrasound probe to a user.

In an ultrasound probe of an electron scanning type, a plurality of elements included in an ultrasound transducer are driven at a time to acquire data of a sound ray. Accordingly, even if a sensitivity decrease occurs in one element, influence on an image is small. It is difficult for a user to determine the sensitivity decrease from viewing the image.

Under such a situation, for example, JP H09-527 discloses a technique including a circuit that detects an abnormal state for each transmission and reception channel of an ultrasound probe, the technique determining possibility of diagnosis when the abnormal state is detected and displaying a determination result. In this technique, information concerning a channel in the abnormal state is displayed by characters and informed to a user.

JP 2009-178262 A discloses a technique for determining, based on a reception signal obtained from a predetermined vibrating element for evaluation of an ultrasound probe, whether a sensitivity characteristic of the vibrating element for evaluation is normal, generating, based on a result of the determination, characteristic distribution data indicating a distribution of sensitivity characteristics of a plurality of vibrating elements, and determining possibility of diagnosis. In this technique, a display unit displays a vibrating element determined as abnormal to be distinguishable from a normal vibrating element to thereby inform an abnormal part of the ultrasound probe to a user.

SUMMARY

In some embodiments, provided is an ultrasound imaging system configured to generate data of an ultrasound image based on an echo signal received from each of a plurality of elements included in an ultrasound transducer that transmit and receive ultrasound. The ultrasound imaging system includes: a determining circuit configured to determine, using a signal corresponding to the echo signal obtained by receiving from each of the plurality of elements, concerning the elements, whether a decrease in reception sensitivity occurs; and a control circuit configured to cause, based on a position of an element where the determining circuit determines that the decrease in the reception sensitivity occurs, a display to display at least one of display data indicating an image region where sensitivity decreases in the ultrasound image and information for informing that a sensitivity decreased element in which a decrease in reception sensitivity occurs is present. The determining circuit is configured to acquire sensitivity information of the plurality of elements, extract an element having the sensitivity information smaller than a first threshold as a candidate element serving as a candidate of the sensitivity decreased element, and determine, using a statistical value of sensitivity information of a predetermined number of elements located in a near field region of the candidate element, whether a decrease in reception sensitivity occurs in the candidate element.

In some embodiments, provided is an operating method of an ultrasound imaging system configured to generate data of an ultrasound image based on an echo signal received from each of a plurality of elements included in an ultrasound transducer that transmit and receive ultrasound. The operating method includes: determining, using a signal corresponding to the echo signal obtained by receiving from each of the plurality of elements, concerning the elements, whether a decrease in reception sensitivity occurs; and causing, based on a position of an element where the determining determines that the decrease in the reception sensitivity occurs, a display to display at least one of display data indicating an image region where sensitivity decreases in the ultrasound image and information for informing that a sensitivity decreased element in which a decrease in reception sensitivity occurs is present. The determining includes acquiring sensitivity information of the plurality of elements, extracting an element having the sensitivity information smaller than a first threshold as a candidate element serving as a candidate of the sensitivity decreased element, and determining, using a statistical value of sensitivity information of a predetermined number of elements located in a near field region of the candidate element, whether a decrease in reception sensitivity occurs in the candidate element.

In some embodiments, provided is a non-transitory computer-readable recording medium with an executable program stored thereon. The program causes an ultrasound imaging system configured to generate data of an ultrasound image based on an echo signal received from each of a plurality of elements included in an ultrasound transducer that transmit and receive ultrasound, to execute: determining, using a signal corresponding to the echo signal obtained by receiving from each of the plurality of elements, concerning the elements, whether a decrease in reception sensitivity occurs; and causing, based on a position of an element where the determining determines that the decrease in the reception sensitivity occurs, a display to display at least one of display data indicating an image region where sensitivity decreases in the ultrasound image and information for informing that a sensitivity decreased element in which a decrease in reception sensitivity occurs is present. The determining includes acquiring sensitivity information of the plurality of elements, extracting an element having the sensitivity information smaller than a first threshold as a candidate element serving as a candidate of the sensitivity decreased element, and determining, using a statistical value of sensitivity information of a predetermined number of elements located in a near field region of the candidate element, whether a decrease in reception sensitivity occurs in the candidate element.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes for carrying out the disclosure "hereinafter referred to as "embodiments") are explained below with reference to the accompanying drawings.

First Embodiment

Figure 1:
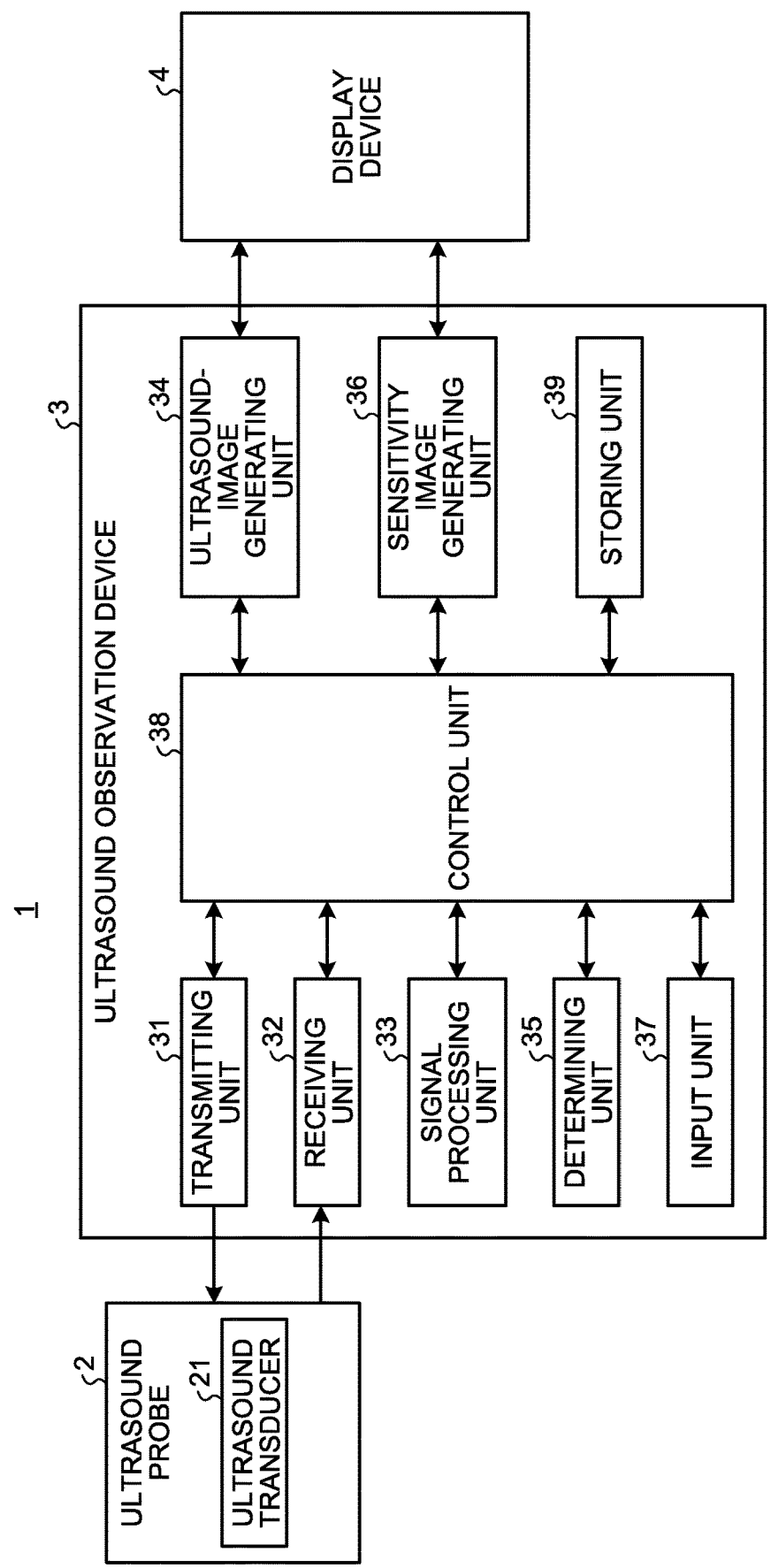
FIG. 1 is a block diagram illustrating a configuration of an ultrasound diagnosis system including an ultrasound observation device according to a first embodiment of the disclosure.

FIG. 1 is a block diagram illustrating a configuration of an ultrasound diagnosis system including an ultrasound observation device according to a first embodiment of the disclosure. An ultrasound diagnosis system 1 illustrated in the figure includes an ultrasound probe 2 that transmits ultrasound to a subject, which is an observation target, and receives the ultrasound reflected on the subject, an ultrasound observation device 3 that generates an ultrasound image based on an ultrasound signal acquired by the ultrasound probe 2, and a display device 4 that displays the ultrasound image generated by the ultrasound observation device 3.

The ultrasound probe 2 includes, at the distal end portion thereof, an ultrasound transducer 21 that converts an electric pulse signal received from the ultrasound observation device 3 into an ultrasound pulse (an acoustic pulse) and irradiates the ultrasound pulse on the subject and converts an ultrasound echo reflected on the subject into an electric echo signal (an ultrasound signal) represented by a voltage change and outputs the echo signal. The ultrasound transducer 21 is an electron scanning type including a plurality of elements arranged in an array shape. The element is configured using a piezoelectric body of lead zirconate titanate (PZT), lead titanate (PT), lead niobate, or the like and performs conversion of mechanical energy and electric energy to thereby transmit and receive ultrasound. In the following explanation, the ultrasound transducer 21 of a radial type is explained. However, this is only an example. The ultrasound transducer 21 may be a convex type or a linear type.

The ultrasound probe 2 may be an ultrasound endoscope further including an imaging optical system and an imaging element or may be a thin miniature probe not including an optical system. The ultrasound probe 2 may be not only a type inserted into the body of a subject but also an external type that irradiates ultrasound from the body surface of a subject.

The ultrasound observation device 3 includes a transmitting unit 31, a receiving unit 32, a signal processing unit 33, an ultrasound-image generating unit 34, a determining unit 35, a sensitivity image generating unit 36, an input unit 37, a control unit 38, and a storing unit 39.

The transmitting unit 31 is electrically connected to the ultrasound probe 2 and transmits a transmission signal (a pulse signal) to the ultrasound transducer 21. A frequency band of the pulse signal transmitted by the transmitting unit 31 is desirably set to a wideband that substantially covers a linear response frequency band of electroacoustic conversion of the pulse signal into an ultrasound pulse in the ultrasound transducer 21. The transmitting unit 31 transmits the transmission signal to a plurality of elements forming one sound ray while controlling transmission timings to the elements. The plurality of elements, which receive the transmission signal in this way, irradiate ultrasound beams. The transmitting unit 31 transmits various control signals output by the control unit 38 to the ultrasound probe 2. Note that power of a transmission signal transmitted by the transmitting unit 31 when an element having decreased sensitivity (a sensitivity decreased element) is detected may be set higher compared with power of a transmission signal during an examination.

The receiving unit 32 receives an echo signal, which is an electric reception signal, from the ultrasound transducer 21 and A/D-converts the echo signal to thereby generate data of a digital radio frequency (RF) signal (hereinafter referred to as RF data). The receiving unit 32 also has a function of receiving various kinds of information including an ID for identification from the ultrasound probe 2.

The signal processing unit 33 generates digital reception data for ultrasound image based on the RF data received from the receiving unit 32. Specifically, the signal processing unit 33 applies publicly-known processing such as digital beam forming (DBF) for adjusting and adding up phases of a plurality of RF data, envelope detection processing, and logarithmic conversion processing and generates digital reception data for ultrasound image. The reception data for ultrasound image includes a plurality of line data (sound ray data) in which amplitude or intensity of an echo signal indicating intensity of reflection of an ultrasound pulse are arranged along a transmission and reception direction (a depth direction) of the ultrasound pulse. The signal processing unit 33 outputs the generated reception data for ultrasound image for one frame to the ultrasound-image generating unit 34.

The ultrasound-image generating unit 34 generates ultrasound image data based on the reception data for ultrasound image received from the signal processing unit 33. The ultrasound-image generating unit 34 includes a digital scan converter (DSC) that convers the reception data for ultrasound image into data conforming to a display scheme of the display device 4. The ultrasound-image generating unit 34 further performs publicly-known signal processing such as gain processing and contrast processing to thereby generate ultrasound image data. The ultrasound image data is so-called B-mode image data. The B-mode image data is a gray scale image in which values of red (R), green (G), and blue (B), which are variables in the case in which an RGB color system is adopted as a color space, are matched.

The determining unit 35 analyzes the RF data received from the receiving unit 32 to thereby determine whether the elements included in the ultrasound transducer 21 are sensitivity decreased elements. The determining unit 35 detects the amplitude of the RF data as a sensitivity value and thereafter compares the sensitivity value with a predetermined threshold and determines an element having a sensitivity value smaller than the threshold as an element in which a decrease in reception sensitivity occurs (hereinafter referred to as sensitivity decreased element). The determining unit 35 writes, for example, sensitivity information setting the element determined as the sensitivity decreased element to 1 and setting the other elements to 0 in the storing unit 39 and causes the storing unit 39 to store the sensitivity information.

Figure 2:
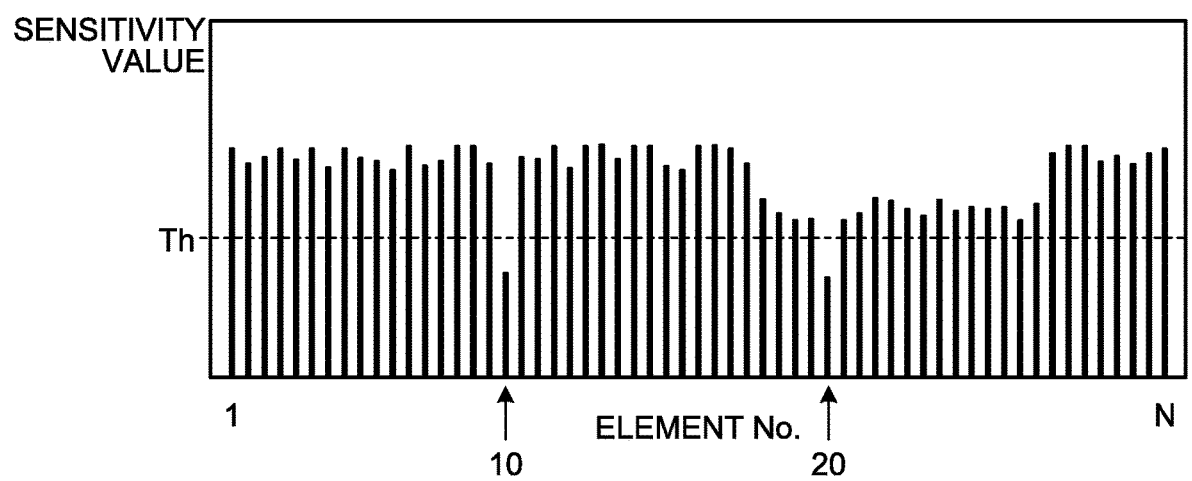
FIG. 2 is a diagram illustrating an overview of determination processing performed by a determining unit of the ultrasound observation device according to the first embodiment of the disclosure.

FIG. 2 is a diagram illustrating an overview of determination processing of the determining unit 35. In FIG. 2, sensitivity values of N (N: integer) elements included in the ultrasound transducer 21 are respectively illustrated. In the case illustrated in FIG. 2, elements with element numbers n=10 and 20 have sensitivities smaller than a sensitivity threshold Th. Therefore, in the case illustrated in FIG. 2, the determining unit 35 determines the element with the element number 10 (hereinafter referred to as element 10) and the element with the element number 20 (referred to as element 20) as sensitivity decreased elements. This determination processing has an object of determining whether the elements are sensitivity decreased elements before an examination of a subject by the ultrasound diagnosis system 1 is performed. This determination processing is performed in a state in which, after a user connects the ultrasound probe 2 to the ultrasound observation device 3, the user holds the distal end portion of the ultrasound probe 2 in the air. When the distal end portion of the ultrasound probe 2 is present in the air, the echo signal received by the receiving unit 32 in response to the transmission signal transmitted by the transmitting unit 31 is an echo signal reflected on a boundary surface between the ultrasound transducer 21 and the air and returned.

The sensitivity image generating unit 36 performs processing such as coordinate conversion into a coordinate corresponding to an ultrasound image using sensitivity information of each element stored by the storing unit 39 to thereby generate, based on the position of the sensitivity decreased element, display data indicating an image region where sensitivity decreases in the ultrasound image. An image displayed by the display device according to this display data (hereinafter referred to as sensitivity image) is an image in which the positions of the elements in the ultrasound transducer 21 are the same as those in the ultrasound image.

Figure 3:
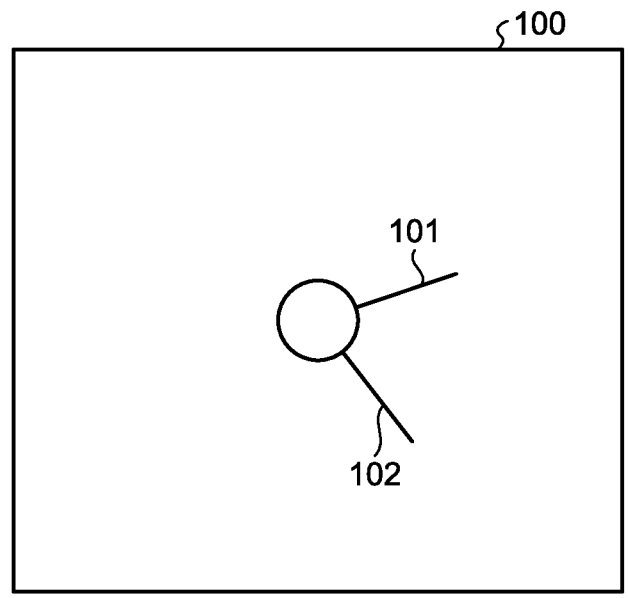
FIG. 3 is a diagram illustrating a display example of a sensitivity image displayed by a display device.

FIG. 3 is a diagram illustrating a display example of the sensitivity image displayed by the display device 4. A sensitivity image 100 illustrated in the figure is an image generated according to the detection result illustrated in FIG. 2. Sensitivity decreased parts 101 and 102 respectively corresponding to the positions of two elements determined as the sensitivity decreased elements by the determining unit 35 are displayed. Note that the sensitivity image 100 may be displayed with white and black reversed in FIG. 3 according to the ultrasound image. The sensitivity decreased parts 101 and 102 may be displayed in a predetermined color other than black.

Figure 4:
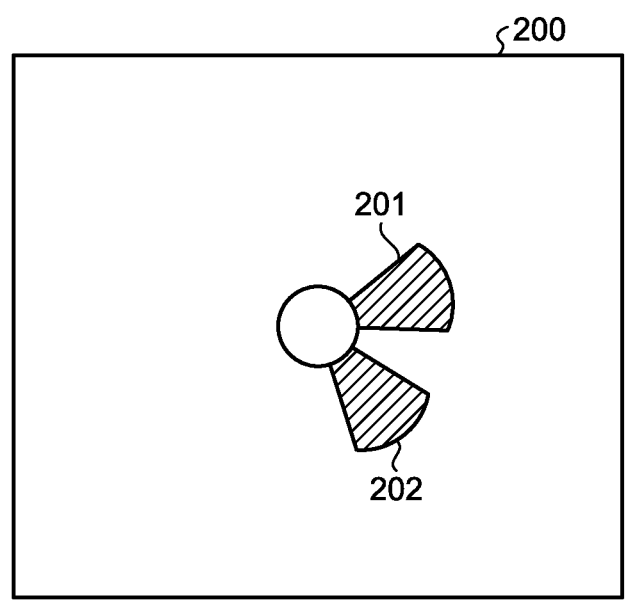
FIG. 4 is a diagram illustrating another display example of the sensitivity image displayed by the display device.

FIG. 4 is a diagram illustrating another display example of the sensitivity image displayed by the display device 4. A sensitivity image 200 illustrated in the figure is an image generated according to the detection result illustrated in FIG. 2. Image regions affected by the two elements determined as the sensitivity decreased elements by the determining unit 35 are displayed as sensitivity decreased parts 201 and 202. Note that the sensitivity image 200 may be displayed with white and black reversed in FIG. 4 according to the ultrasound image. The sensitivity decreased parts 201 and 202 may be painted out with a predetermined color and displayed or may be painted out with a predetermined pattern and displayed.

Even when the sensitivity decreased parts are displayed by lines as illustrated in FIG. 3, when an adjacent plurality of elements are sensitivity decreased elements, those lines are sometimes connected to be the same display as regions illustrated in FIG. 4.

The user, who views the sensitivity image 100 or 200, can intuitively grasp the positions of the sensitivity decreased parts in the ultrasound image.

The input unit 37 is configured using a user interface such as a keyboard, a button, a mouse, a trackball, a touch panel, or a touch pad and receives inputs of various operation signals. As one of the various operation signals, a signal for instructing a start of sensitivity determination processing for the elements of the ultrasound transducer 21 is included.

The control unit 38 reads out information stored by the storing unit 39 from the storing unit 39 and executes various kinds of arithmetic processing relating to an operating method for the ultrasound observation device 3 to thereby collectively control the operation of the ultrasound diagnosis system 1 including the ultrasound observation device 3.

The storing unit 39 stores information such as a threshold of a sensitivity value referred to in the determination by the determining unit 35 and a result of determination for each of the elements by the determining unit 35. The threshold of the sensitivity value stored by the storing unit 39 may be different depending on a type of the ultrasound probe 2. The storing unit 39 stores various programs for operating the ultrasound diagnosis system 1, data including various parameters necessary for the operation of the ultrasound diagnosis system 1, and the like. The various programs include an operating program for executing the operating method for the ultrasound diagnosis system 1. The various programs can also be widely distributed while being stored in a computer-readable storage medium such as a hard disk, a flash memory, a CD-ROM, a DVD-ROM, or a flexible disk. The various programs can also be acquired by being downloaded via a communication network. The communication network referred to herein is realized by, for example, an existing public line network, a local area network (LAN), or a wide area network (WAN) and may be either wired or wireless.

The ultrasound observation device 3 having the configuration explained above is realized using a general-purpose processor such as a central processing unit (CPU) or a dedicated integrated circuit or the like that executes a specific function such as an application specific integrated circuit (ASIC) or an field programmable gate array (FPGA), a read only memory (ROM) in which various programs and the like are installed in advance, and a RAM (Random Access Memory) or the like that stores operation parameters, data, and the like for respective kinds of processing.

The display device 4 receives data signals of the ultrasound image and the sensitivity image generated by the ultrasound observation device 3 via a video cable and displays the data signals. The display device 4 is configured using a monitor of liquid crystal, organic electro luminescence (EL), or the like.

Figure 5:
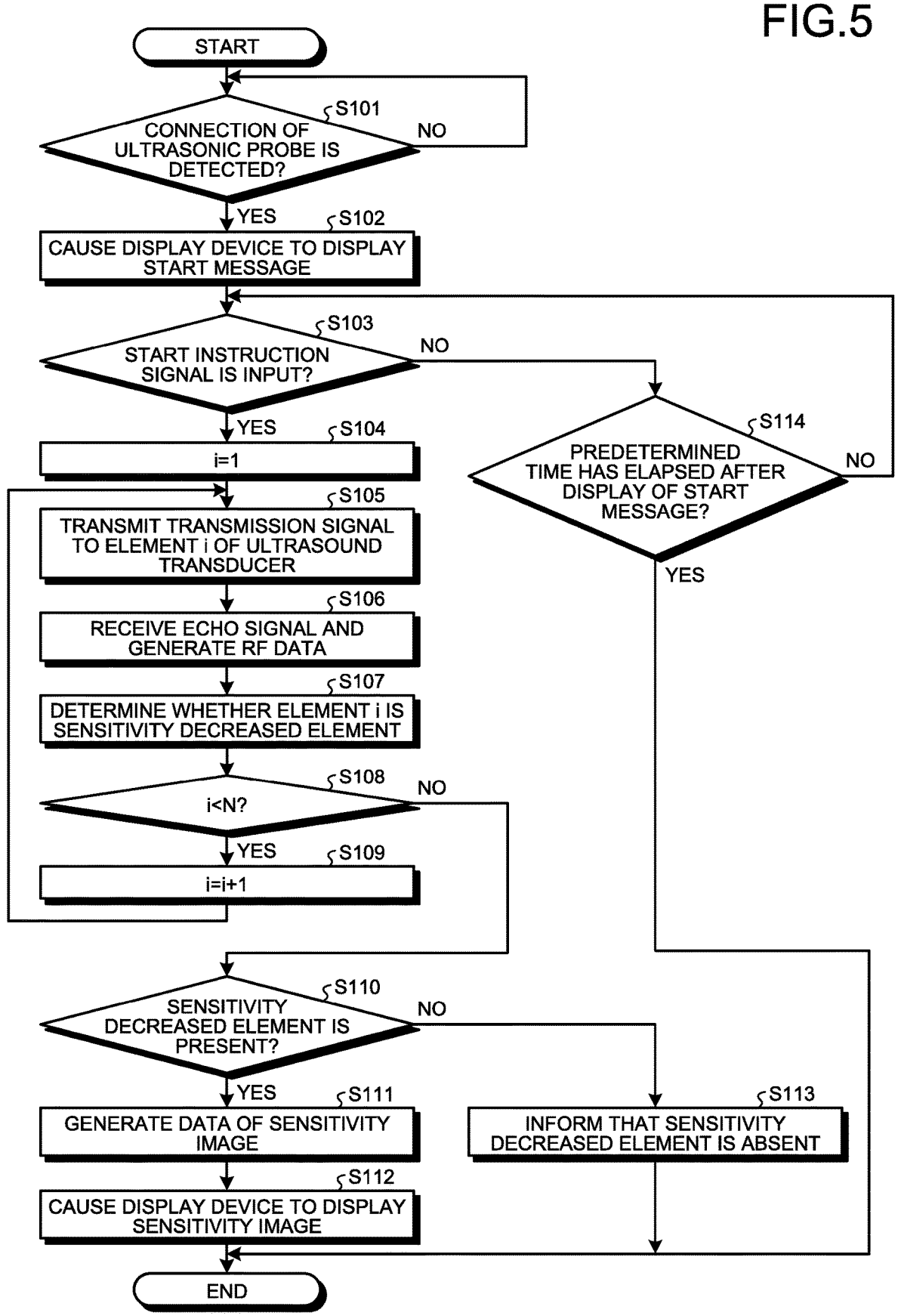
FIG. 5 is a flowchart illustrating an overview of element sensitivity determination processing performed by the ultrasound observation device according to the first embodiment of the disclosure.

FIG. 5 is a flowchart illustrating an overview of element sensitivity determination processing performed by the ultrasound observation device 3 having the configuration explained above. In the flowchart explained below, it is assumed that a power supply of the ultrasound observation device 3 is in a turned-on state.

When the ultrasound probe 2 is connected to a connector of the ultrasound observation device 3, the receiving unit 32 receives a signal from the ultrasound probe 2, and the control unit 38 detects the connection of the ultrasound probe 2 (step S101: Yes), the control unit 38 causes the display device 4 to display a start message for the element sensitivity determination processing (step S102). This start message has, for example, content "Start the element sensitivity determination processing for the elements of the ultrasound probe. Please press an OK button in a state in which the distal end portion of the ultrasound probe is kept in the air". When the control unit 38 does not detect the connection of the ultrasound probe 2 (step S101: No), the ultrasound observation device 3 repeats step S101.

Thereafter, when the input unit 37 receives an input of a start instruction signal (step S103: Yes), the control unit 38 sets a counter i to an initial value 1 (step S104). Subsequently, the transmitting unit 31 selects an element with an element number i (hereinafter referred to as element i) among the plurality of elements included in the ultrasound transducer 21 and transmits a transmission signal to the element i (step S105). Note that, in the above explanation, when the input unit 37 receives the input of the start instruction signal, the transmitting unit 31 transmits the transmission signal to the element 1. However, the transmitting unit 31 may automatically start to transmit the transmission signal to the element 1 when the control unit 38 detects the connection of the ultrasound probe 2.

Subsequently, the receiving unit 32 receives an echo signal from the ultrasound transducer 21, A/D-converts the echo signal to thereby generate RF data, and outputs the RF data to the determining unit 35 (step S106).

The determining unit 35 determines, using the RF data received from the receiving unit 32, whether the element i is a sensitivity decreased element and causes the storing unit 39 to store sensitivity information corresponding to a determination result (step S107). The determining unit 35 calculates a sensitivity value of the element i from the amplitude of the RF data and, when the sensitivity value is lower than a threshold, determines the element i as the sensitivity decreased element. In the case illustrated in FIG. 2, the determining unit 35 determines the two elements 10 and 20 as sensitivity decreased elements.

Thereafter, the control unit 38 determines whether the counter i is smaller than the number N of elements (step S108). When the counter i is smaller than N (step S108: Yes), since the determination processing for all the elements has not ended, the control unit 38 increases the counter i by 1 (step S109) and performs control for returning to step S105. On the other hand, when the counter i is not smaller than N (step S108: No), since the determination processing for all the elements has ended, the control unit 38 performs control for shifting to step S110.

Processing in step S110 and subsequent steps is explained. When the sensitivity decreased element is present as a result of the determination by the determining unit 35 (step S110: Yes), the sensitivity image generating unit 36 refers to the storing unit 39 and generates data of a sensitivity image (step S111). Subsequently, the control unit 38 causes the display device 4 to display the sensitivity image (step S112). The display device 4 displays, for example, the sensitivity image 100 illustrated in FIG. 3 or the sensitivity image 200 illustrated in FIG. 4. In this case, the control unit 38 may cause the display device 4 to display, together with the sensitivity image, a message for informing that the sensitivity decreased element is present. After step S112, the ultrasound observation device 3 ends a series of processing.

Note that, after step S112, when the input unit 37 receives an input of a signal for instructing erasing of the sensitivity image, the control unit 38 may cause the display device 4 to end the display of the sensitivity image. After a predetermined time elapses from the start of the display of the sensitivity image by the display device 4, the control unit 38 may cause the display device 4 to end the display of the sensitivity image.

When the sensitivity decreased element is absent as a result of the determination by the determining unit 35 (step S110: No), the control unit 38 causes the display device 4 to display a message for informing that the sensitivity decreased element is absent (step S113). Note that, in this case, instead of causing the display device 4 to display the message, the control unit 38 may inform the absence of the sensitivity decreased element using means for outputting sound or means for flashing a lamp. After step S113, the ultrasound observation device 3 ends a series of processing.

When the input unit 37 does not receive the input of the start instruction signal in step S103 (step S103: No), when the predetermined time has elapsed from the start of the display of the start message (step S114: Yes), the ultrasound observation device 3 ends a series of processing. When the predetermined time has not elapsed in step S114 (step S114: No), the ultrasound observation device 3 returns to step S103.

According to the first embodiment of the disclosure explained above, the display data indicating the image region where the sensitivity decreases in the ultrasound image is generated based on the position of the element determined as the sensitivity decreased element in which the decrease in the reception sensitivity occurs. Therefore, the user can intuitively grasp the influence on the ultrasound image due to the sensitivity decrease of the ultrasound element included in the ultrasound probe.

Second Embodiment

An ultrasound observation device according to a second embodiment of the disclosure is different from the ultrasound observation device in the first embodiment in element sensitivity determination processing in a determining unit. A configuration of an ultrasound diagnosis system according to the second embodiment is the same as the configuration in the first embodiment. In the following explanation, components of the ultrasound diagnosis system are denoted by the same reference numerals and signs as those in the first embodiment.

Figure 6:
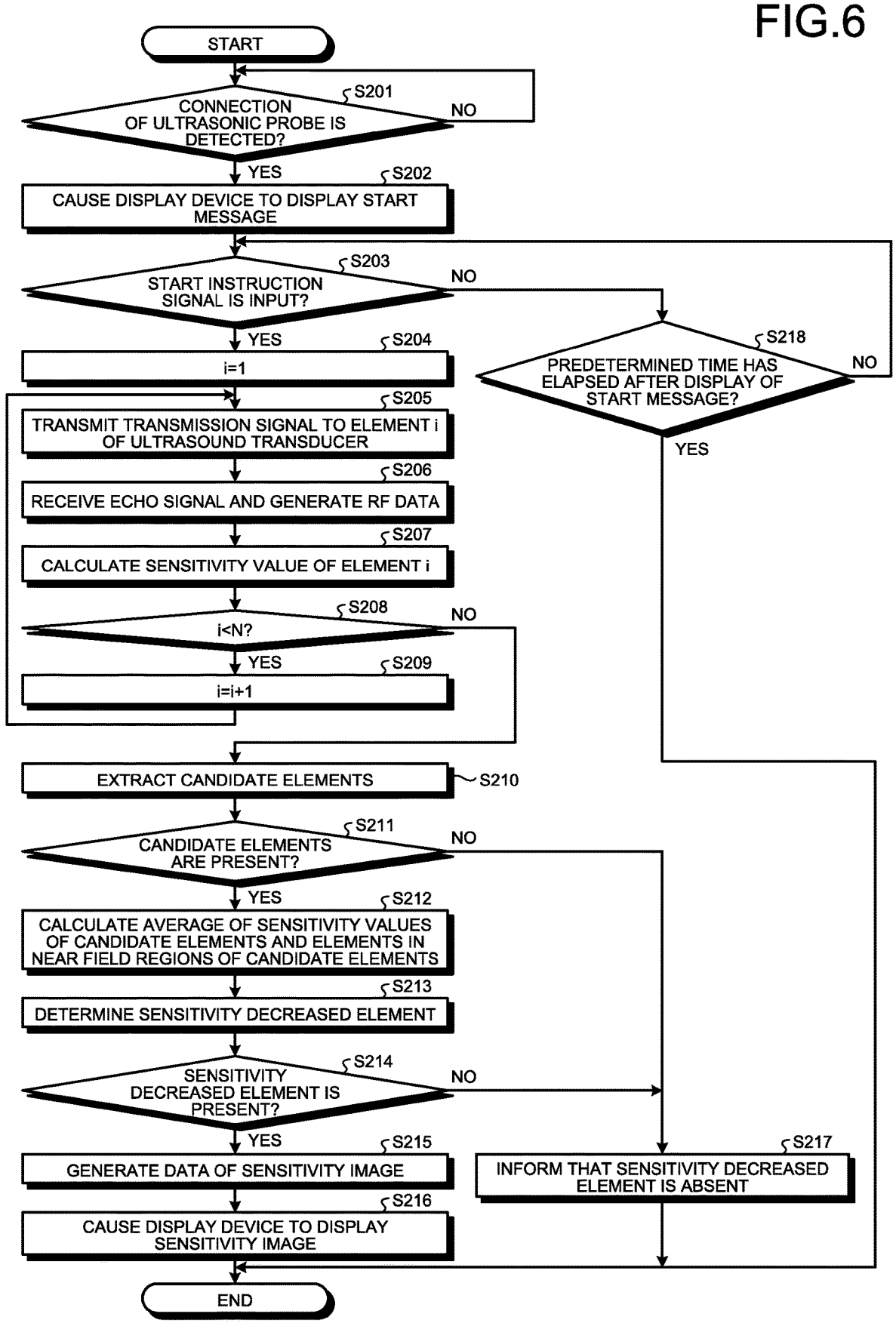
FIG. 6 is a flowchart illustrating an overview of element sensitivity determination processing performed by an ultrasound observation device according to a second embodiment of the disclosure.

FIG. 6 is a flowchart illustrating an overview of element sensitivity determination processing performed by the ultrasound observation device according to the second embodiment. Processing in steps S201 to S206 respectively corresponds to the processing in steps S101 to S106 explained in the first embodiment.

In step S207, the determining unit 35 calculates a sensitivity value of the element i using the RF data received from the receiving unit 32 and causes the storing unit 39 to store the sensitivity value (step S207). Thereafter, the control unit 38 determines whether the counter i is smaller than the number N of the elements (step S208). When the counter i is smaller than N (step S208: Yes), the control unit 38 increases the counter i by 1 (step S209) and performs control for returning to step S205. On the other hand, when the counter i is not smaller than N (step S208: No), the control unit 38 performs control for shifting to step S210.

In step S210, the determining unit 35 compares sensitivity values of the elements with the threshold Th and extracts elements having sensitivity values smaller than the threshold Th as candidate elements serving as candidates of sensitivity decreased elements (step S210). When the determining unit 35 extracts the candidate elements (step S211: Yes), the determining unit 35 reads out sensitivity values of elements in near field regions of the candidate elements from the storing unit 39 and calculates an average of sensitivity values of the read-out elements and the candidate elements (step S212).

Figure 7:
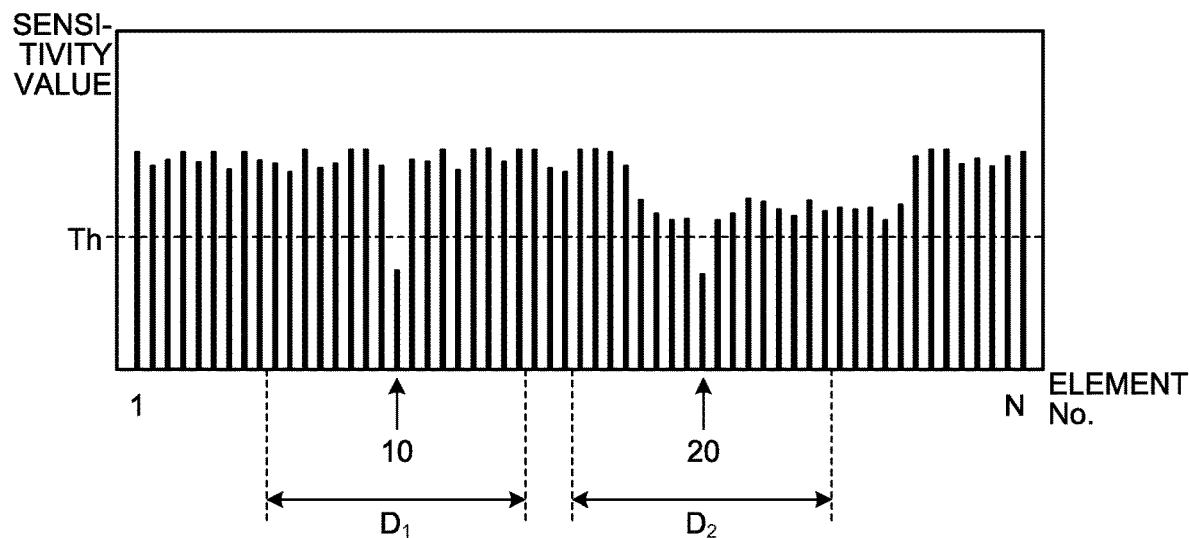
FIG. 7 is a diagram for explaining near field regions.

FIG. 7 is a diagram for explaining the near field regions. In FIG. 7, as in FIG. 2, sensitivity values of the N elements included in the ultrasound transducer 21 are respectively illustrated. Sensitivity values of the element 10 and the element 20 are smaller than the threshold Th. In this case, the determining unit 35 extracts the element 10 and the element 20 as candidate elements, sets, as near field regions, regions including a predetermined number of elements centering on the candidate elements, and calculates an average of sensitivity values of elements in the near field regions. In the case illustrated in FIG. 7, a sensitivity value of a near field region $D_1$ of the element 10 is relatively higher than a sensitivity value of a near field region $D_2$ of the element 20. Therefore, an average of sensitivity values of elements in the near field region $D_1$ is larger than an average of sensitivity values of elements in the near field region $D_2$.

For example, the number of elements included in the near field regions may be set to a transmission numerical aperture set for generating an ultrasound image or may be set to a number close to the transmission numerical aperture. Such the number of the elements is given as a function of the transmission numerical aperture. Note that the elements included in the near field regions may be not all of elements in a region and, for example, may be thinned out at a predetermined interval in the region or may be selected by a predetermined number at random in the region. The sensitivity values of the candidate elements may not be included in sensitivity values of elements used for calculating the average.

Subsequently, the determining unit 35 determines, as a sensitivity decreased element, a candidate element, a calculated average of sensitivity values of elements in a near field region of which is smaller than a second threshold (step S213). The second threshold at this time may be the same as the threshold Th or may be different from the threshold Th.

When the sensitivity decreased element is present as a result of the determination (step S214: Yes), the sensitivity image generating unit 36 generates data of a sensitivity image (step S215). In the case illustrated in FIG. 7, for example, when the average of the sensitivity values of the elements in the near field region $D_1$ is larger than the second threshold and, on the other hand, the average of the sensitivity values of the elements in the near field region $D_2$ is smaller than the second threshold, the determining unit 35 determines, as a sensitivity decreased element, only the element 20 of the two candidate elements.

Thereafter, the control unit 38 causes the display device 4 to display the sensitivity image (step S216). In FIG. 7, a display example of the sensitivity image in the case in which only the element 20 is determined as the sensitivity decreased element is an image obtained by deleting a sensitivity decreased part 101 from the sensitivity image 100 illustrated in FIG. 3 and an image obtained by deleting a sensitivity decreased part 201 from the sensitivity image 200 illustrated in FIG. 4. After step S216, the ultrasound observation device 3 ends a series of processing.

Note that, after step S216, when the input unit 37 receives an input of a signal for instructing erasing of the sensitivity image, the control unit 38 may cause the display device 4 to end the display of the sensitivity image. After a predetermined time elapses after the display of the sensitivity image by the display device 4, the control unit 38 may cause the display device 4 to end the display of the sensitivity image.

When the sensitivity decreased element is absent as a result of the determination by the determining unit 35 (step S214: No), the control unit 38 causes the display device 4 to display a message for informing that the sensitivity decreased element is absent (step S217). After step S217, the ultrasound observation device 3 ends a series of processing.

When the determining unit 35 does not extracts candidate elements in step S211 (step S211: No), the control unit 38 performs control for shifting to step S217.

When the input unit 37 does not receive the input of the start instruction signal in step S203 (step S203: No), when the predetermined time has elapsed from the start of the display of the start message (step S218: Yes), the ultrasound observation device 3 ends a series of processing. When the predetermined time has not elapsed in step S218 (step S218: No), the ultrasound observation device 3 returns to step S203.

According to the second embodiment explained above, as in the first embodiment, the user can intuitively grasp the influence on the ultrasound image due to the sensitivity decrease of the ultrasound element included in the ultrasound probe.

According to the second embodiment, it is determined according to the sensitivity information of the elements included in the near field region with respect to the candidate elements of the sensitivity decreased element whether the element is the sensitivity decreased element. Therefore, it is possible to more accurately detect the sensitivity decreased part that causes influence on the ultrasound image.

Note that, instead of the average of the sensitivity values of the near field region determined by the determining unit 35, a statistical value such as a sum, dispersion, or a mode of the sensitivity values in the near field region may be calculated. In that case, a second threshold corresponding to the statistical value only has to be set. A value of the second threshold may be changed according to the number of elements forming a population. Consequently, even at an end portion of the ultrasound transducer 21 having a small numerical aperture used, it is possible to accurately detect a sensitivity decreased part that affects an image.

First Modification of Second Embodiment

Figure 8:
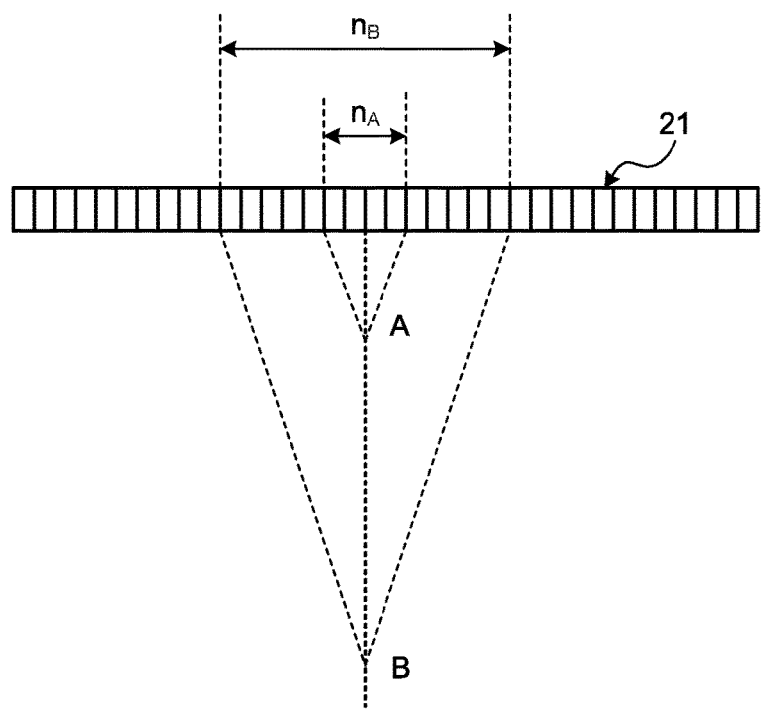
FIG. 8 is a diagram illustrating an example of a setting method for the near field regions.
Figure 9:
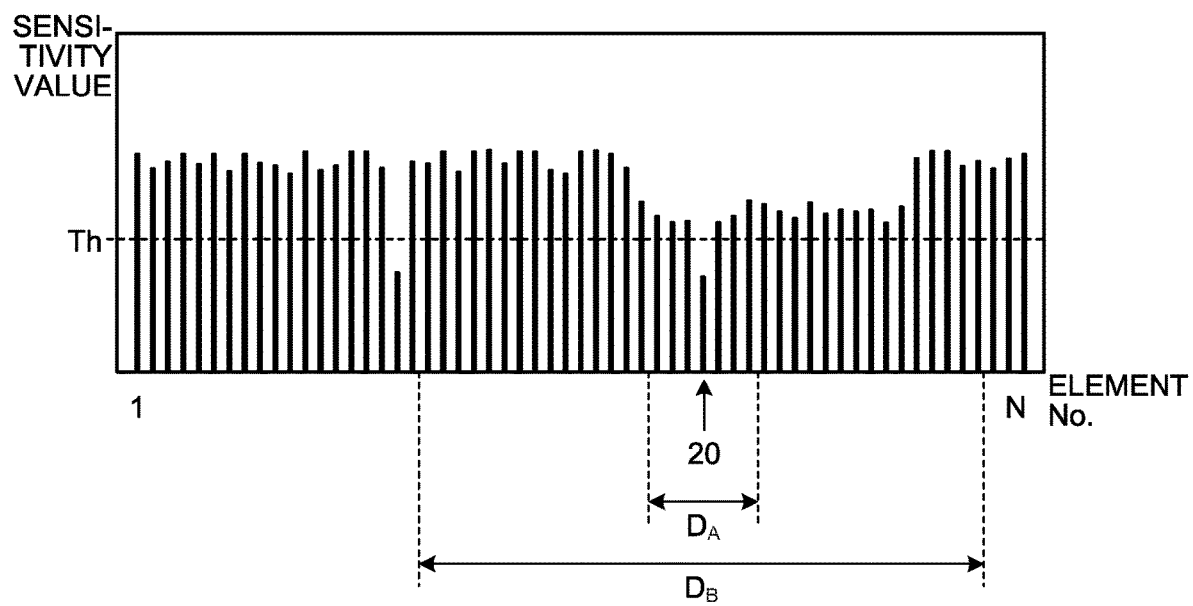
FIG. 9 is a diagram for explaining that near field regions of candidate elements are changed according to depth.

A near field region may be set according to a reception numerical aperture in generating an ultrasound image. As illustrated in FIG. 8, the reception numerical aperture is sometimes set larger as depth that ultrasound reaches is larger. Accordingly, the number of elements in near field regions may be set larger as the depth is larger. FIG. 9 is a diagram for explaining that near field regions of candidate elements are changed according to the depth. In the first modification, the second threshold used for determination by the determining unit 35 may be set according to the depth.

Figure 10:
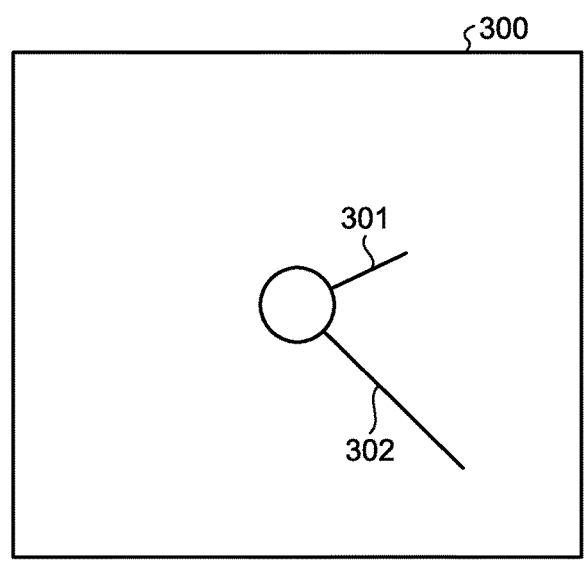
FIG. 10 is a diagram illustrating a display example of a sensitivity image in a first modification of the second embodiment of the disclosure.

FIG. 10 is a diagram illustrating a display example of a sensitivity image in the first modification. A sensitivity image 300 illustrated in the figure displays two sensitivity decreased parts 301 and 302. The sensitivity decreased part 301 and the sensitivity decreased part 302 have different line lengths. This indicates that, in the sensitivity decreased part 302, a deeper region is affected by a sensitivity decrease than in the sensitivity decreased part 301. The user can grasp, by viewing the sensitivity image 300, a range of a depth direction affected by the sensitivity decrease in addition to the sensitivity decreased position.

According to the first modification explained above, the near field regions are set according to the depth and presence or absence of a sensitivity decrease is determined for each depth. Therefore, it is possible to provide more detailed and more highly accurate sensitivity decrease information.

Figure 11:
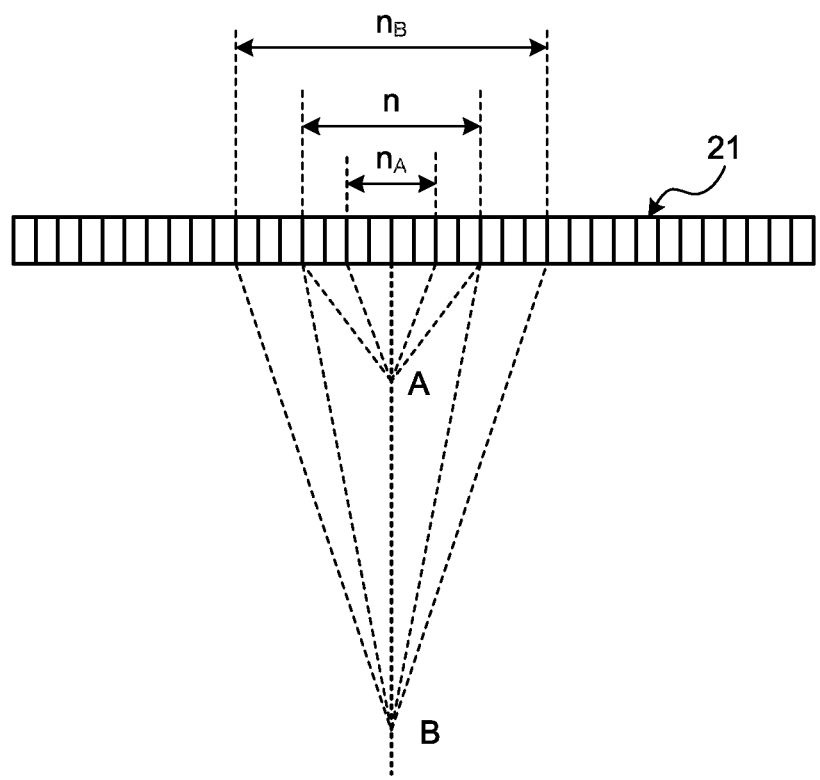
FIG. 11 is a diagram illustrating another example of the setting method for the near field regions.

Note that the near field regions may be set based on a magnitude relation between the reception numerical aperture and the transmission numerical aperture. As illustrated in FIG. 11, during ultrasound image generation, in some case, the transmission numerical aperture is fixed and the reception numerical aperture is changed according to the depth. In such a case, the near field regions for each depth may be set using a smaller value of the transmission numerical aperture and the reception numerical aperture.

Second Modification of Second Embodiment

Figure 12:
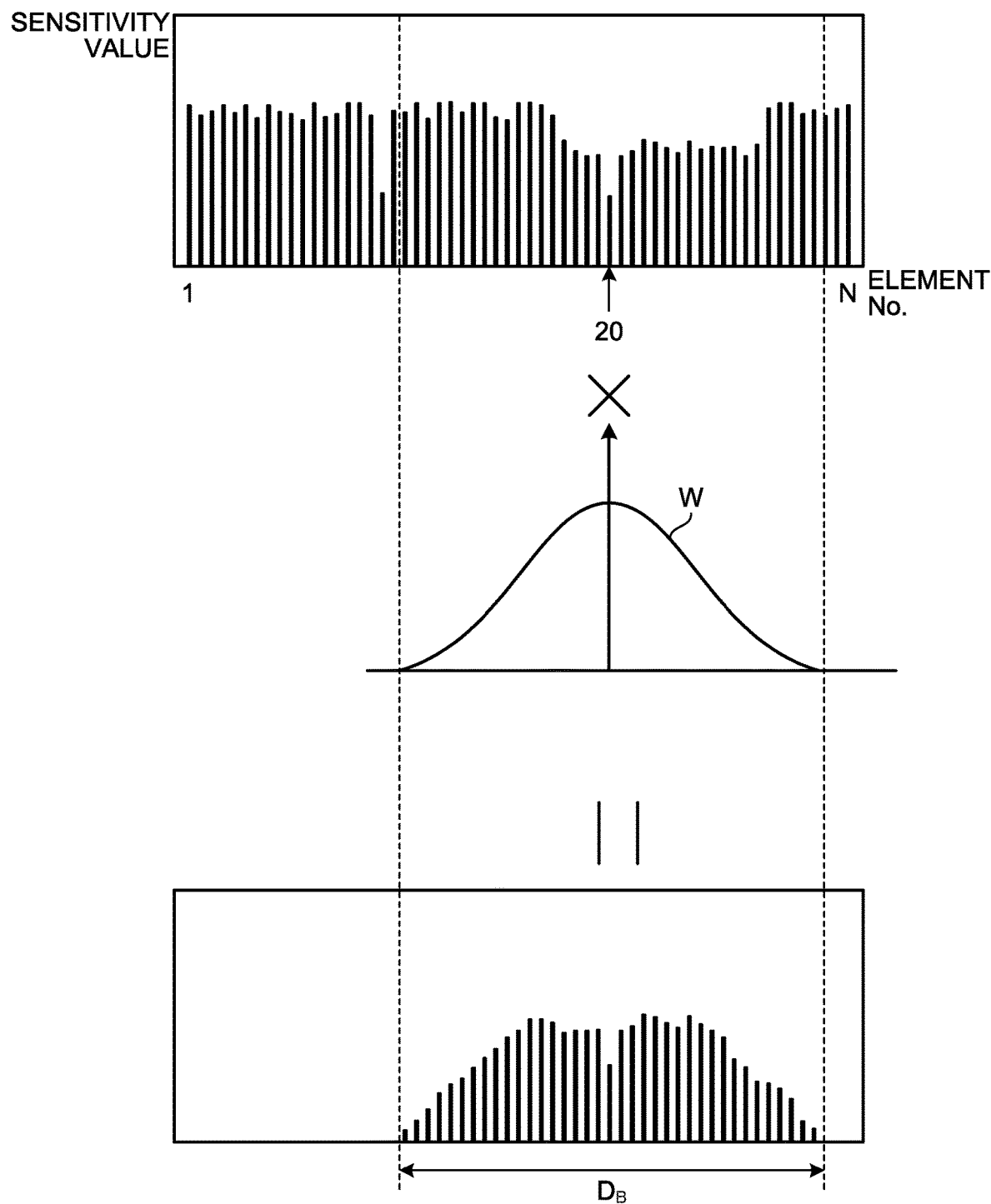
FIG. 12 is a diagram illustrating an overview of processing of a determining unit in a second modification of the second embodiment of the disclosure.

When the determining unit 35 calculates the statistical value such as the average of the sensitivity values of the near field regions, the determining unit 35 may weigh the statistical value taking into account directivity of the elements. FIG. 12 is a diagram illustrating an overview of processing of the determining unit 35 in the second modification. The determining unit 35 multiplies the sensitivity values of the near field regions by a weight coefficient and calculates the statistical value such as the average with respect to a result of the multiplication. A weight coefficient W has a large value in the center of the near field region, that is, near the candidate element and has a smaller value further away from the candidate element.

According to the second modification explained above, since the determination of the sensitivity decreased element is performed using the weighted sensitivity values, it is possible to perform determination reflecting contribution of the elements included in the near field regions.

Third Embodiment

An ultrasound observation device according to a third embodiment of the disclosure performs, using an ultrasound beam irradiated when an ultrasound image is generated, determination processing for determining whether elements are sensitivity decreased elements. A configuration of an ultrasound diagnosis system according to this third embodiment is the same as the configuration in the first embodiment. In the following explanation, components of the ultrasound diagnosis system are denoted by the same reference numerals and signs as those in the first embodiment.

Figure 13:
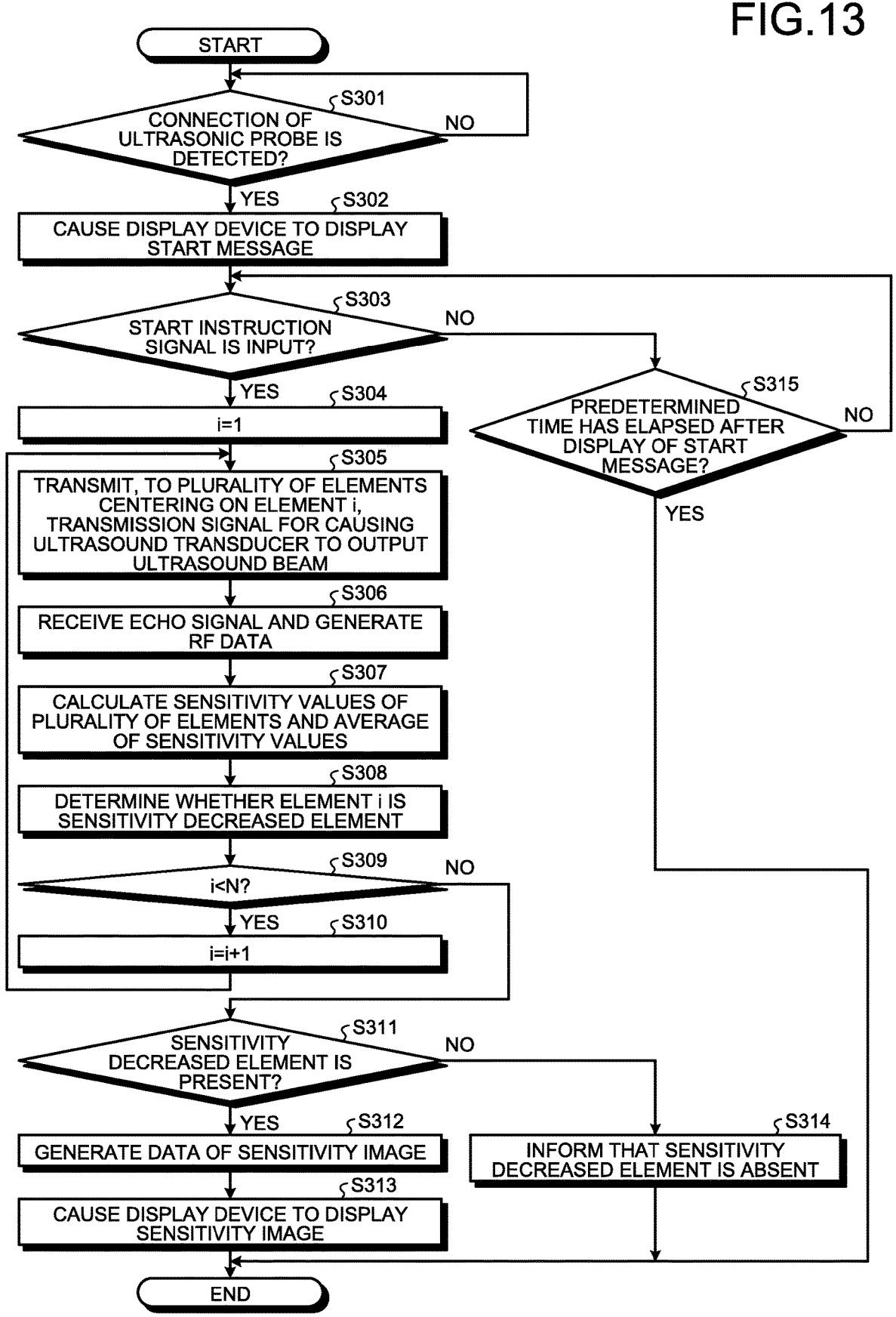
FIG. 13 is a flowchart illustrating an overview of element determination processing performed by an ultrasound observation device according to a third embodiment of the disclosure.

FIG. 13 is a flowchart illustrating an overview of element determination processing performed by the ultrasound observation device according to the third embodiment. Processing in steps S301 to S304 respectively corresponds to the processing in steps S101 to S104 explained in the first embodiment.

In step S305, the transmitting unit 31 transmits, in order to cause the ultrasound transducer 21 to output an ultrasound beam, a transmission signal to a plurality of elements equivalent to a transmission numerical aperture centering on the element i while controlling transmission timings (step S305).

Subsequently, the receiving unit 32 receives an echo signal from the ultrasound transducer 21 and A/D-converts the echo signal to thereby generate RF data, and outputs the RF data to the determining unit 35 (step S306).

The determining unit 35 calculates sensitivity values of the plurality of elements using the RF data received from the receiving unit 32, calculates an average of the sensitivity values, and causes the storing unit 39 to store the average (step S307).

Thereafter, the determining unit 35 compares the average of the sensitivity values and a threshold to thereby determine whether the element i is a sensitivity decreased element and causes the storing unit 39 to store a determination result (step S308).

Subsequently, the control unit 38 determines whether the counter i is smaller than the number N of the elements (step S309). When the counter i is smaller than N (step S309: Yes), the control unit 38 increases the counter i by 1 (step S310) and performs control for returning to step S305. On the other hand, when the counter i is not smaller than N (step S309: No), the control unit 38 performs control for shifting to step S311.

Processing in steps S311 to S315 respectively corresponds to steps S110 to S114 explained in the first embodiment.

In this third embodiment, a display form of a sensitivity image is the same as the sensitivity image 100 (see FIG. 3) explained in the first embodiment. However, in the case of this third embodiment, the sensitivity decreased parts 101 and 102 are equivalent to a sound ray of an ultrasound image.

According to the third embodiment of the disclosure explained above, as in the first embodiment, the user can intuitively grasp the influence on the ultrasound image due to the sensitivity decrease of the ultrasound element included in the ultrasound probe.

Other Embodiments

The modes for carrying out the disclosure are explained above. However, the disclosure should not be limited by only the embodiments explained above. For example, instead of calculating the sensitivity values using the RF data, the determining unit 35 may calculate an average of luminance values of the pixels after the RF data is converted into an image by the same processing as the processing for the ultrasound image and use the average as sensitivity information to thereby determine presence or absence of a sensitivity decrease of the elements.

The display device 4 may be able to display the sensitivity decreased part while an examination is performed using the ultrasound diagnosis system 1. For example, when the input unit 37 receives an input of a signal for instructing the display of the sensitivity decreased part during the examination, the sensitivity image generating unit 36 specifies a sensitivity decreased element referring to the storing unit 39 and generates data of a sensitivity image according to the display of the ultrasound image. When the ultrasound image is scrolled, the sensitivity image generating unit 36 also changes a display form of the sensitivity image according to the scroll. The control unit 38 causes the display device 4 to display the sensitivity image and the ultrasound image side by side. Note that the control unit 38 may cause the display device 4 to display the sensitivity image to be smaller than the ultrasound image. Thereafter, when the input unit 37 receives an input of a signal for deleting the display of the sensitivity decreased part, the control unit 38 causes the display device 4 to end the display of the sensitivity image.

The ultrasound observation device may further include a superimposed-image generating unit that generates data of a superimposed image obtained by superimposing the ultrasound image and the sensitivity image. In this case, when the input unit 37 receives a display instruction input for the sensitivity decreased part during the examination, after the sensitivity image generating unit 36 generates data of a sensitivity image as explained above, the superimposed-image generating unit superimposes the data on data of an ultrasound image to generate data of a superimposed image. The superimposed image may give visual information such as a color, chroma, brightness, a design, or a pattern to the sensitivity decreased part and display the sensitivity decreased part or may increase the transmittance of the sensitivity decreased part and display the sensitivity decreased part semi-transparently.

Since the ultrasound observation device has a function of displaying the sensitivity decreased part even during the examination, the user can grasp the sensitivity decreased part even during the examination and make use of the sensitivity decreased part in the examination and diagnosis.

According to the disclosure, the user is capable of intuitively grasp influence on the ultrasound image due to the sensitivity decrease of the ultrasound element included in the ultrasound probe.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound imaging system configured to generate data of an ultrasound image based on an echo signal received from each of a plurality of elements included in an ultrasound transducer that transmit and receive ultrasound, the ultrasound imaging system comprising:
a determining circuit configured to determine, using a signal corresponding to the echo signal obtained by receiving from each of the plurality of elements, concerning the elements, whether a decrease in reception sensitivity occurs; and
a control circuit configured to cause, based on a position of an element where the determining circuit determines that the decrease in the reception sensitivity occurs, a display to display at least one of display data indicating an image region where sensitivity decreases in the ultrasound image and information for informing that a sensitivity decreased element in which a decrease in reception sensitivity occurs is present, wherein
the determining circuit is configured to
acquire sensitivity information of the plurality of elements,
extract an element having the sensitivity information smaller than a first threshold as a candidate element serving as a candidate of the sensitivity decreased element, and
determine, using a statistical value of sensitivity information of a predetermined number of elements located in a near field region of the candidate element, whether a decrease in reception sensitivity occurs in the candidate element.

2. The ultrasound imaging system according to claim 1, wherein, when an average of the sensitivity information of the predetermined number of elements is smaller than a second threshold, the determining circuit is configured to determine that the decrease in the reception sensitivity occurs in the candidate element.

3. The ultrasound imaging system according to claim 2, wherein, the second threshold is set according to a number of the predetermined number of elements.

4. The ultrasound imaging system according to claim 1, wherein the predetermined number is a number relating to either a transmission numerical aperture or a reception numerical aperture of the ultrasound transducer.

5. The ultrasound imaging system according to claim 4, wherein the predetermined number is set to a different number depending on depth that the ultrasound reaches.

6. The ultrasound imaging system according to claim 1, wherein the sensitivity information is either a sensitivity value obtained based on amplitude of the echo signal or a luminance value at a time when the echo signal is converted into an image.

7. The ultrasound imaging system according to claim 1, wherein the determining circuit is configured to perform determination based on a reference of different sensitivity information according to depth that the ultrasound reaches.

8. The ultrasound imaging system according to claim 1, wherein the determining circuit is configured to determine, based on a condition decided for each type of an ultrasound probe connected to the ultrasound imaging system, whether the decrease in the reception sensitivity occurs in the elements.

9. The ultrasound imaging system according to claim 1, wherein the determining circuit is configured to perform determination when connection of an ultrasound probe is detected.

10. The ultrasound imaging system according to claim 1, wherein the signal corresponding to the echo signal is a signal for generating the data of the ultrasound image.

11. The ultrasound imaging system according to claim 2, wherein, when an average obtained by weighting the sensitivity information of the predetermined number of elements according to a position of the candidate element is smaller than the second threshold, the determining circuit is configured to determine that the decrease in the reception sensitivity occurs in the candidate element.

12. An operating method of an ultrasound imaging system configured to generate data of an ultrasound image based on an echo signal received from each of a plurality of elements included in an ultrasound transducer that transmit and receive ultrasound, the operating method comprising:
- determining, using a signal corresponding to the echo signal obtained by receiving from each of the plurality of elements, concerning the elements, whether a decrease in reception sensitivity occurs; and
- causing, based on a position of an element where the determining determines that the decrease in the reception sensitivity occurs, a display to display at least one of display data indicating an image region where sensitivity decreases in the ultrasound image and information for informing that a sensitivity decreased element in which a decrease in reception sensitivity occurs is present, wherein the determining includes
- acquiring sensitivity information of the plurality of elements,
- extracting an element having the sensitivity information smaller than a first threshold as a candidate element serving as a candidate of the sensitivity decreased element, and
- determining, using a statistical value of sensitivity information of a predetermined number of elements located in a near field region of the candidate element, whether a decrease in reception sensitivity occurs in the candidate element.

13. A non-transitory computer-readable recording medium with an executable program stored thereon, the program causing an ultrasound imaging system configured to generate data of an ultrasound image based on an echo signal received from each of a plurality of elements included in an ultrasound transducer that transmit and receive ultrasound, to execute:
- determining, using a signal corresponding to the echo signal obtained by receiving from each of the plurality of elements, concerning the elements, whether a decrease in reception sensitivity occurs; and
- causing, based on a position of an element where the determining determines that the decrease in the reception sensitivity occurs, a display to display at least one of display data indicating an image region where sensitivity decreases in the ultrasound image and information for informing that a sensitivity decreased element in which a decrease in reception sensitivity occurs is present, wherein the determining includes
- acquiring sensitivity information of the plurality of elements,
- extracting an element having the sensitivity information smaller than a first threshold as a candidate element serving as a candidate of the sensitivity decreased element, and
- determining, using a statistical value of sensitivity information of a predetermined number of elements located in a near field region of the candidate element, whether a decrease in reception sensitivity occurs in the candidate element.

* * * * *